United States Patent
Venuto, Sr.

(10) Patent No.: US 6,554,208 B1
(45) Date of Patent: Apr. 29, 2003

(54) TANNING BOOTH HAVING AUTOMATED SPRAY

(75) Inventor: Ralph Venuto, Sr., Blackwood, NJ (US)

(73) Assignee: Hollywood Tanning Systems, Inc., Mt. Laurel, NJ (US)

( * ) Notice: Subject to any disclaimer, the term of this patent is extended or adjusted under 35 U.S.C. 154(b) by 0 days.

(21) Appl. No.: 10/038,856

(22) Filed: Jan. 8, 2002

Related U.S. Application Data

(60) Provisional application No. 60/331,715, filed on Nov. 21, 2001.

(51) Int. Cl.$^7$ .................. B05B 15/10; A61M 35/00
(52) U.S. Cl. ............................... 239/207; 604/289
(58) Field of Search ........................ 13/333; 4/536, 4/525; 239/120, 207, 104; 601/156, 160, 166; 604/289, 290

(56) References Cited

U.S. PATENT DOCUMENTS

| | | |
|---|---|---|
| 624,420 A | 5/1899 | Atwater et al. |
| 870,766 A | 11/1907 | Eaton |
| 871,074 A | 11/1907 | Stockton |
| 1,262,638 A | 4/1918 | Class |
| 1,982,509 A | 11/1934 | Frank |
| 2,700,384 A | 1/1955 | Ivory |
| 2,949,403 A | 8/1960 | Andreadis |
| 3,009,165 A | 11/1961 | Washam et al. |
| 3,396,411 A | 8/1968 | Vieceli |
| 3,734,058 A | 5/1973 | Hightower et al. |
| 3,867,906 A | 2/1975 | Johnson |
| 3,868,950 A | 3/1975 | Kato |
| 3,932,151 A | 1/1976 | Lau |
| 4,020,796 A | 5/1977 | Grifa |
| 4,056,078 A | 11/1977 | Blafford et al. |
| 4,083,328 A | 4/1978 | Baker |
| 4,196,479 A | 4/1980 | Geisler |

(List continued on next page.)

FOREIGN PATENT DOCUMENTS

| | | |
|---|---|---|
| GB | 2241 165 | 2/1991 |
| WO | WO/94/12146 | 6/1994 |

OTHER PUBLICATIONS

JEPTO 5–4/:349–351, "Non–Carcinogenicty of Dihydroxyacetone by Skin Painting," Frank J. Akin and Edward Marlowe, Dept. of Pharmacology and Toxicology, Schering–Plough Corp.
Federal Register, vol. 38, No. 148, Aug. 2, 1973, pp. 20615–20616, Part 8—Color Additives.
Cosmetology and Perfumery, vol. 88, Aug. 1973, pp. 30–33, Dr. E. Forman."Theory and practice of artificial tanning, a literature and patent survey.".
Dermatology 1994:188:247, J.A. Johnson, R.M. Fusaro, Dept. of Internal Medicine/Dermatology, Univ. of Nebraska Med. Ctr., "Persistence of Skin Color and Fluorescence after Treatement with Dihydroxyacetone.".
"Formulating Effective Self–Tanners with DHA," Thekla Kurz, Ph.D., E. Merck/Rona, Darmstadt, Germany.
Binks, Training Division, TD49–2R–4, "Spray Application Processes," 4 pp.
Clinical Reviews, "Dihydroxyacetone–containing sunless or self–tanning lotions," Stanley B. Levy, MD, Chapel Hill, NC, pp. 989–993.

*Primary Examiner*—Todd E. Manahan
(74) *Attorney, Agent, or Firm*—Blank Rome LLP

(57) ABSTRACT

A spray chamber has a spray system and a ventilation system. The spray system includes a compressor and stationary spray jets that are positioned 360° about a user, from head to toe. The spray system operates in a spray mode and a drying mode. In the spray mode, the composition is sprayed onto the user through the spray jets in the form of a mist. In the drying mode, air is blown through the jets to dry the user. The spray chamber also has a shower spray. In the rinse mode, chlorinated water is emitted from the shower spray to disinfect the spray chamber. The ventilation system includes exhaust fans that operate in the drying mode to draw air and remnant spray mist into a ventilation housing. The spray is filtered to create droplets that are siphoned by a sump pump as waste to a sewer system.

31 Claims, 5 Drawing Sheets

U.S. PATENT DOCUMENTS

| | | |
|---|---|---|
| 4,231,289 A | 11/1980 | Domicent |
| 4,425,672 A | 1/1984 | Johnson et al. |
| 4,510,889 A | 4/1985 | Jobe |
| 4,749,130 A | 6/1988 | Utzinger |
| 4,765,542 A | 8/1988 | Carlson |
| 4,832,943 A | 5/1989 | Grollier et al. |
| 4,862,526 A | 9/1989 | Berger |
| 5,089,269 A | 2/1992 | Noda et al. |
| 5,102,660 A | 4/1992 | Forestier et al. |
| 5,153,174 A | 10/1992 | Band et al. |
| 5,259,339 A | 11/1993 | McLaughlin |
| 5,268,166 A | 12/1993 | Barnett et al. |
| 5,273,214 A | 12/1993 | Huffstutler |
| 5,337,958 A | 8/1994 | Hennessy et al. |
| 5,460,192 A | 10/1995 | McClain |
| 5,493,996 A | 2/1996 | Verschuere et al. |
| 5,664,593 A | 9/1997 | McClain |
| 5,922,333 A | 7/1999 | Laughlin |
| 6,199,557 B1 | 3/2001 | Laughlin |
| 6,302,122 B1 | 5/2001 | Parker et al. |
| 6,251,374 B1 | 6/2001 | Laughlin |
| 6,298,862 B1 | 10/2001 | Laughlin |
| 6,305,384 B2 | 10/2001 | Laughlin |
| 6,387,081 B1 | 5/2002 | Cooper |
| 6,416,747 B1 | 7/2002 | Laughlin |
| 2001/0003283 A1 | 6/2001 | Laughlin |
| 2001/0029961 A1 | 10/2001 | Laughlin |
| 2002/0000236 A1 | 1/2002 | Laughlin |
| 2002/0000237 A1 | 1/2002 | Laughlin |
| 2002/0005208 A1 | 1/2002 | Laughlin |
| 2002/0040721 A1 | 4/2002 | Laughlin |
| 2002/0088475 A1 | 7/2002 | Laughlin |

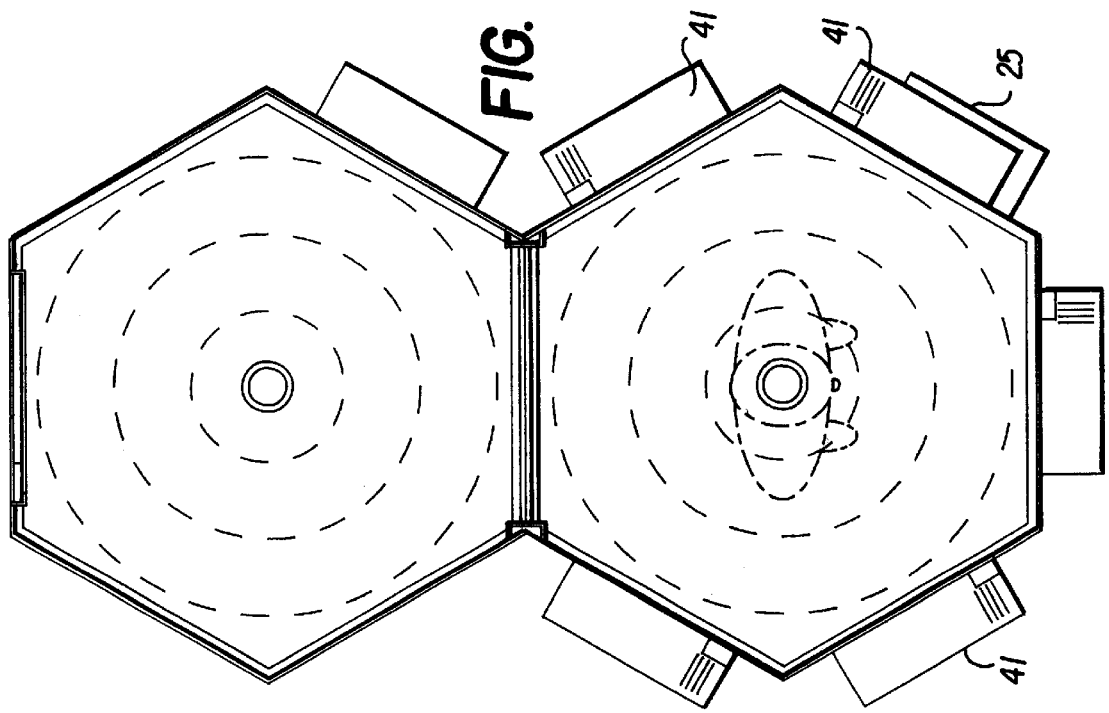
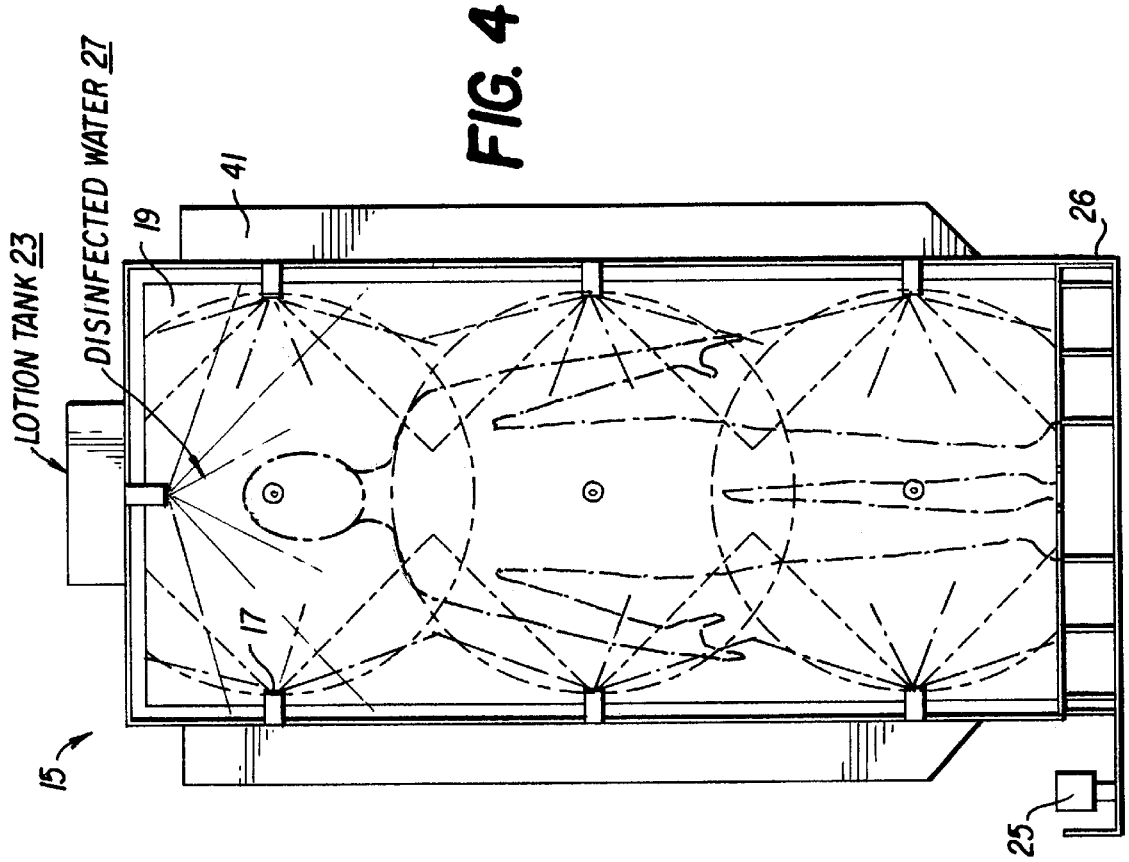

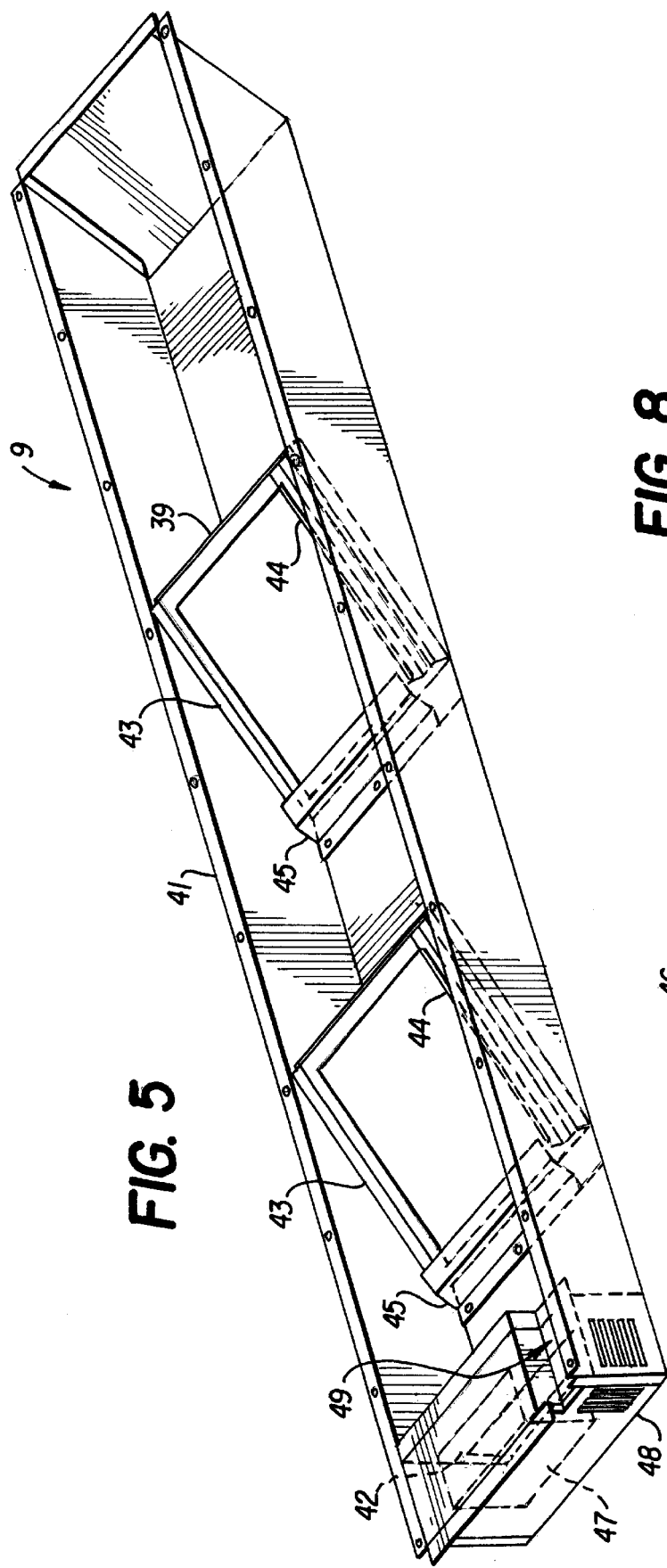
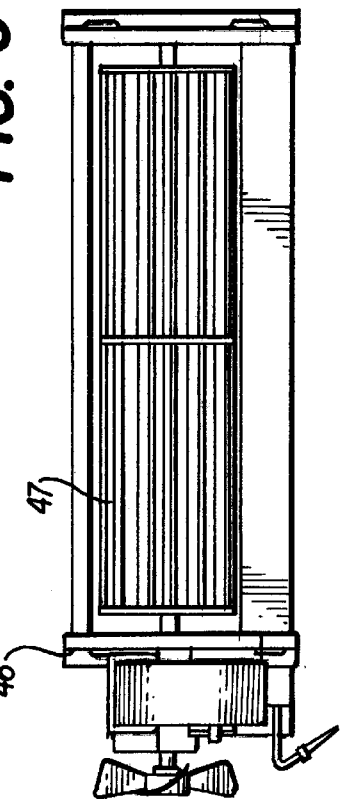

TANNING BOOTH HAVING AUTOMATED SPRAY

RELATED APPLICATION

This application claims priority to provisional application Ser. No. 60/331,715, filed Nov. 21, 2001.

BACKGROUND OF THE INVENTION

Tanning booths have been developed with tanning lamps, so that a user can obtain and maintain a tan all year round, regardless of weather conditions. Tanning booths have proven to be a healthy and effective, and federal guidelines have been established to ensure that tanning booths continue to remain safe. As tanning booths increase in popularity, tanning booth technology continues to improve.

In addition, systems have been developed for coating the human body with chemical compositions. These coating systems are shown, for instance, in U.S. Pat. Nos. 6,305,384, 6,298,862, 6,251,374, 6,199,557, and 5,922,333, all to Laughlin. Common coating compositions include, for instance, self-tanning formulations, suntan lotions, skin toners, skin bleachers, skin lighteners, exfoliants, nutriments, vitamins, massage aides, muscle relaxants, skin treatment agents, burn treatment agents, decontamination agents, cosmetics, wrinkle treatments or removers, moisturizers, preservatives, anti-microbials, thickeners, solvents, emulsifiers, fragrances, stabilizers, sunscreens, surfactants, pH adjusters, anti-caking agents, ingredients to alter the color reaction or oils.

One disadvantage of the prior systems, however, is that they require moving parts, which subject the user to injury if the user comes in contact with those parts. Another disadvantage of the prior coating systems is that they require the user to rotate in order to achieve a complete coating of composition. That movement subjects the user to injury if the user comes in contact with the projections of the spray system, or if the user loses his/her balance.

Movement is especially dangerous due to the presence of chemicals in the air and since the user will often close his/her eyes during application of the composition. In addition, by requiring that the user rotate to achieve a complete application of composition, the prior coating systems are slow and require multiple spray applications (e.g., a front and back application). Yet another disadvantage is that prior systems permit mist to escape from the spray chamber into to the surrounding area (typically a salon).

SUMMARY OF THE INVENTION

Accordingly, it is a primary object of the invention to provide a booth that has a single chamber which coats the user with a composition. It is another primary object of the invention to provide a spray chamber that does not require moving parts in order to achieve a complete and uniform composition coating. It is another object of the invention to provide a spray chamber that provides a complete and uniform composition coating in a single spray application. It is another object of the invention to provide a spray chamber that includes an exhaust system for removing remnant spray mist out of the spray chamber after the user has been sprayed. It is yet another object of the invention to provide a spray chamber with a spray system that disinfects the chamber after each use.

In accordance with these and other objectives, the present invention is a spray chamber having a spray system and a ventilation system. The spray system includes a compressor and stationary spray jets that are positioned 360° about a user, from head to toe. The compressor operates in a spray mode and a drying mode. In the spray mode, the composition is sprayed onto the user through the spray jets in the form of a mist. In the drying mode, air is blown through the jets to dry the user. The spray chamber also includes a shower spray nozzle which, in a rinse mode, emits chlorinated water to clean the spray chamber. The ventilation system includes exhaust fans that operate in the drying mode to draw air and remnant spray mist into a ventilation housing or plenum. The spray is filtered to create droplets that are siphoned by a sump pump as waste to a sewer system.

BRIEF DESCRIPTION OF THE FIGURES

FIG. 4 shows the spray chamber in operation.

FIG. 5 is a perspective drawing of the ventilation housing.

FIG. 6 is a top cutaway view of the booth, showing the ventilation housing.

FIG. 8 is a front view of the fan and motor used in the ventilation housing of FIG. 5.

DETAILED DESCRIPTION OF THE PREFERRED EMBODIMENTS

Figure 3:
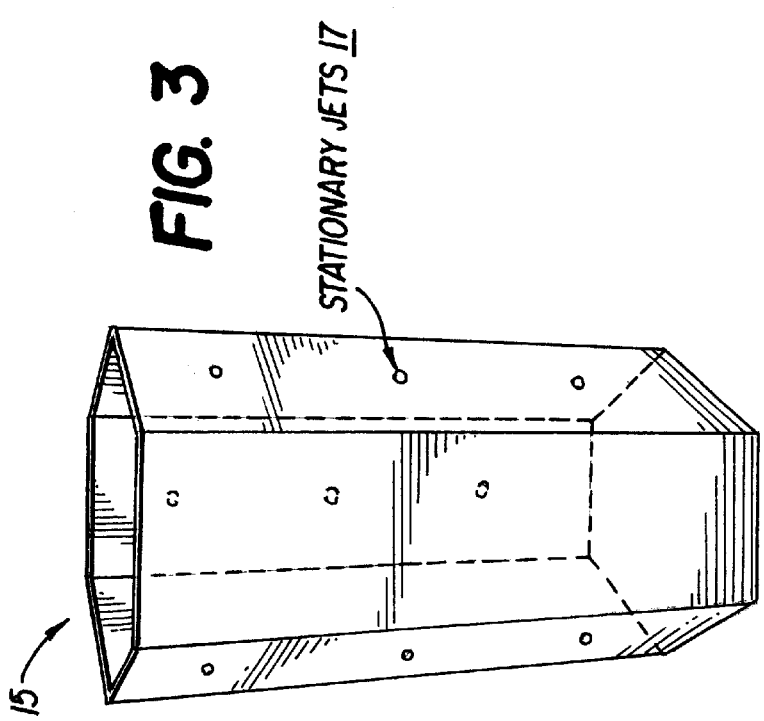
FIG. 3 shows the position of spray jets within the spray chamber of FIG. 1.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

Figure 1:
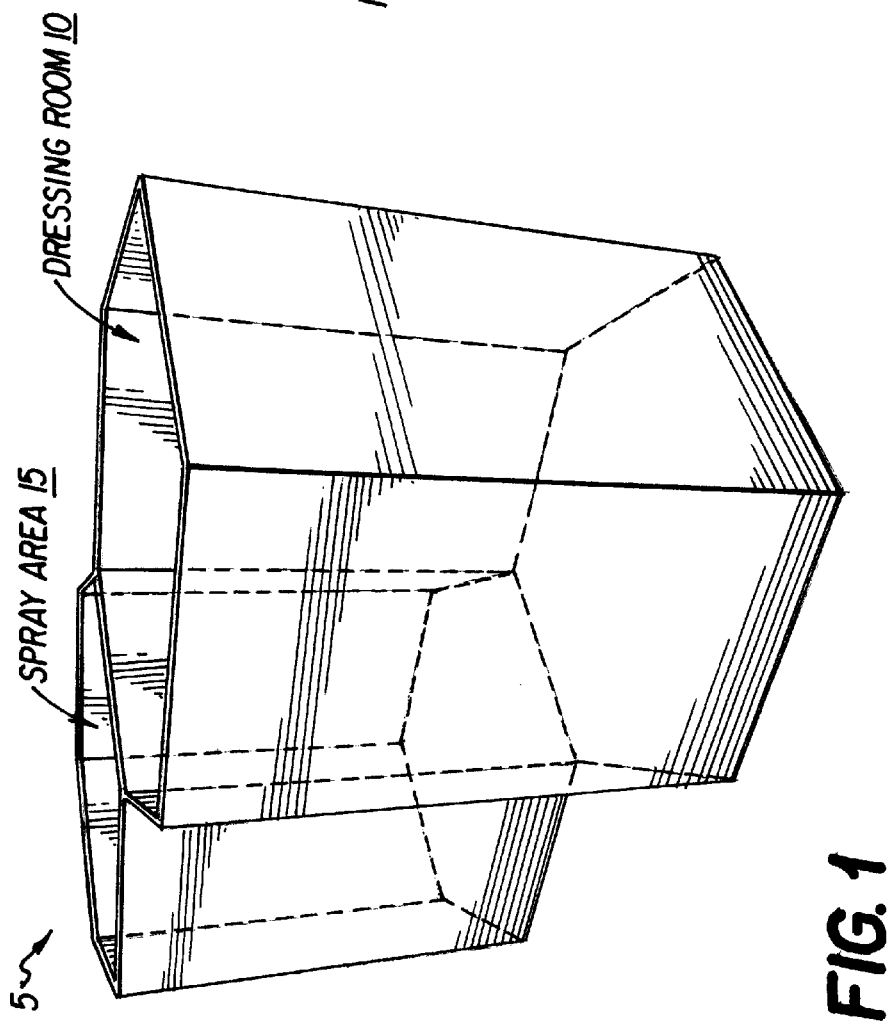
FIG. 1 is a perspective drawing of the booth in accordance with the preferred embodiment of the invention.

Turning to the drawing, FIG. 1 shows a booth 5 of the present invention having a dressing room 10 and a spray chamber 15. The user generally enters the booth 5 through a door (not shown) in one of the walls of the dressing room 10. The dressing room 10 is generally a changing area that provides privacy for the user to dress after exiting the spray room 15 and to undress before entering the spray chamber 15. An interior door separates the dressing room 10 from the spray chamber 15, and allows the user to pass therebetween. The booth 5 can be constructed in accordance with application Ser. No. 09/836,543, filed Apr. 18, 2001, which is hereby incorporated by reference.

The spray chamber 15 has a spray system 7 (FIG. 2) and a ventilation system 9 (FIG. 5). The spray system 7 provides a complete and uniform application of composition to a user. Though the spray system 7 is preferably implemented with the ventilation system 9, the spray system 7 and the ventilation system 9 are separate systems that can be independently used.

Figure 2:
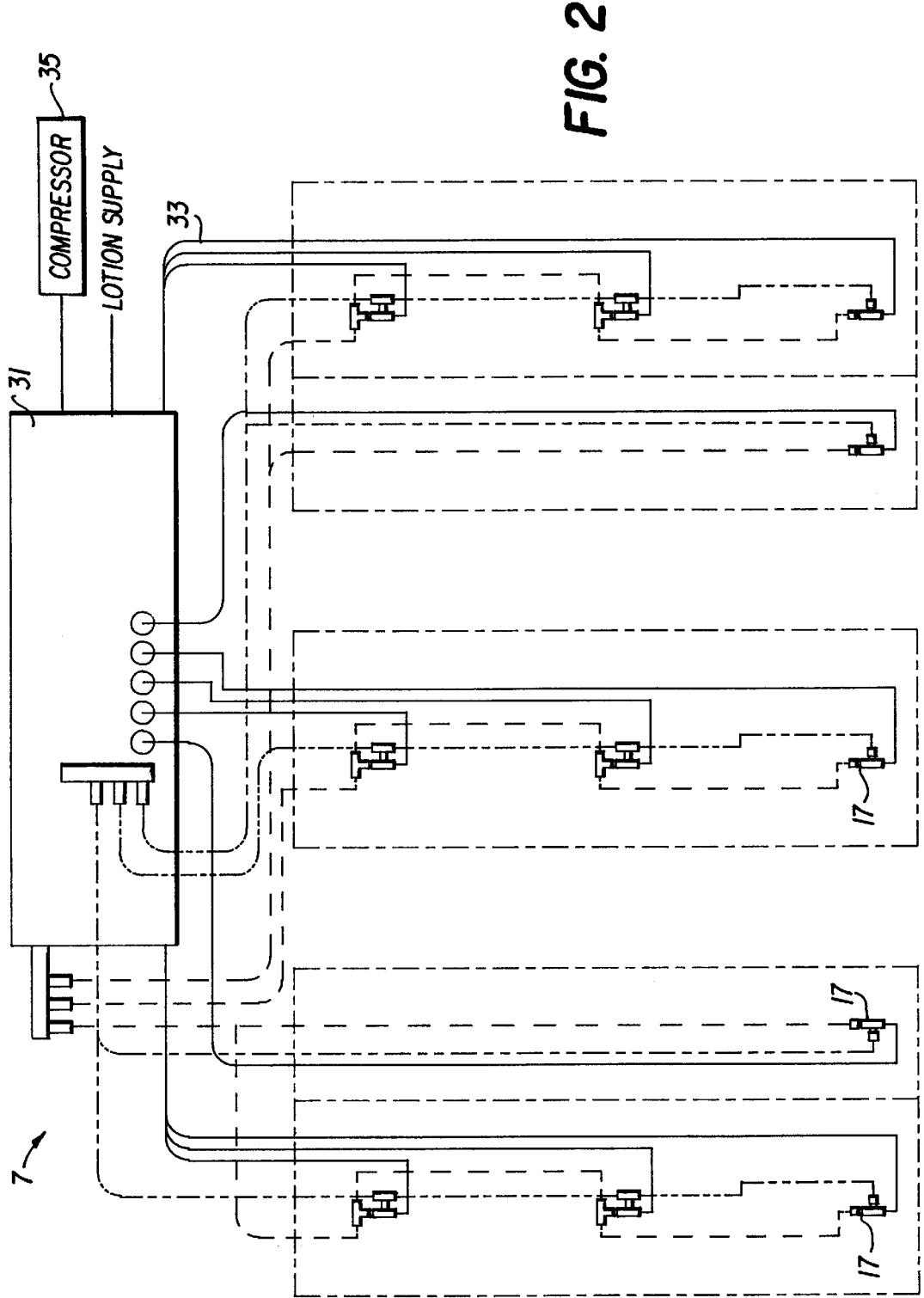
FIG. 2 shows the spray system used with the spray chamber of FIG. 1.

FIGS. 2 and 3 show the preferred arrangement of the stationary spray nozzles or jets 17 located within the spray chamber 15. The spray jets 17 are preferably located in three columns of three jets, plus two extra jets 17 on separate chamber wall panels, for a total of eleven (11) spray jets 17. Each column is positioned vertically on a wall panel of the spray chamber 15. The jets 17 are positioned to provide complete and uniform application of composition to the user in a single treatment, and therefore are located 360° about the user.

The jets 17 also form an upper tier, middle tier and lower tier that cover the user's head and upper body, torso, and lower body, respectively. The two extra jets 17 are provided on the lower tier to provide better coverage of the user's lower body. It should be recognized, however, that any suitable number and positioning of jets 17 can be provided, and the jets 17 need not be vertically or horizontally aligned with each other.

FIG. 2 shows the spray system 7 having spray jets 17, a controller 31, tubing 33, and an air compressor 35. The compressor 35 provides compressed air to the controller 31 via a first tubing 33. The compressor 35 forces the lotion through a second tubing 33 to the nozzles 17, where the first tubing mixes air with the lotion to emit the lotion out through the nozzle 17 in the form of a mist. The compressed air in the first tubing 33 is shown connected to the side of the nozzle connections 17, and the lotion in the second tubing is shown connected to the bottom of the nozzle connections 17. A third tubing also contains compressed air, and is emitted through the nozzles 17 by itself (i.e., without lotion) during a drying mode to dry the user and to clear out the nozzles 17 of any lotion or other blockage. The third tubing 33 is shown connected to the top of the nozzle connections 17.

The spray system 7 operates in a spray mode and a drying mode. In the spray mode, the compressor 35 pumps the composition from a tank 23 (FIG. 4) that is preferably located on the top of the spray chamber 15, through the neoprene tubing 33, to the spray jets 17. FIG. 4 shows composition being expelled in the form of a mist or spray 19 from the jets 17 within the spray chamber 15. The jets 17 apply the composition evenly and completely, and do not require the user to rotate or move about the spray chamber 15. The compressor 35 can be adjusted based upon the type of composition being applied as well as the user's height and size. Preferably, however, the compressor imparts a pressure of between approximately 7–11 psi at each jet 17, and the duration of the spray is about 4–10 seconds. Preferably, the composition is applied as a mist in a single application.

The spray system 7 also operates in an optional evacuation or drying mode. The compressor pumps air through the spray jets 17 to dry the user. The drying mode lasts about 40 seconds, though the duration can be adjusted by the user. The drying mode preferably occurs after the spray mode and is followed by the rinse mode.

The spray chamber 15 also has a shower-type nozzle 27 positioned in the ceiling of the spray chamber 15 (FIG. 4). After the drying mode, the spray chamber 15 can optionally enter a rinse mode. In the rinse mode, chlorinated or disinfected water passes through the shower-type nozzle 27 to clean the spray chamber 15.

In accordance with the preferred embodiment of the invention, the spray system 7 enters the spray mode first to apply the composition, which is then followed by the drying mode and the rinse mode. However, the modes can occur in any order, and the spray system 7 can execute multiple cycles—of spray, dry; spray, dry, rinse—for a single user. In addition, the order of the various modes can be varied depending upon various variables, such as user skin type and the tan the user wishes to achieve. For instance, the system can operate as follows: spray, spray, dry, rinse.

As further shown in FIG. 4, the spray chamber 15 also has housings 41. The housings 41 enclose the tubing 33 located on the exterior of the booth 15, and also comprises the ventilation system 9, which is shown in further detail in FIG. 5. The ventilation system 9 includes housings 41, exhaust fans 47, and a sump pump 25. Importantly, the housing 41 forms a plenum that directs the flow of air and spray from the exhaust fans 47 to the bottom of the spray chamber 15.

The housing 41 has two filters 39 that are held at an angled position by a filter holder 43 and a filter stop 44. The fan 47 draws air and spray 19 into the plenum 41 from the interior of the spray chamber, and down along the plenum housing 41. The air and spray 19 pass through filters 39, which condense the spray mist into droplets. The droplets and air are sucked by the sump pump 25 (FIG. 4) as waste to a sewer line. Excess composition and water passes out through openings in the floor of the spray chamber 15, and the sump pump 25 draws the waste to a sewer line.

An air dam 42 is provided with a rectangular opening. The fan 47 blows air through the rectangular opening, and the air dam 42 prevents the backdraft of lotion mist back into the fan and the interior of the spray chamber. A deflector plate 45 is located at the front end of the filter 39 and deflects mist into the filter 39. A fan cover 49 protects the fan 47 and directs the flow of air into the air dam 42. The fan 47 is operated by a motor that is sealed within a motor chamber 48 to prevent mist from damaging the motor.

The fan 47 and motor are shown in greater detail in FIG. 8. The fan 47 has elongated propellers that align to push air through the rectangular opening in the air dam 42. The motor is cooled by a fan that draws in external air through slots in the motor chamber 48 (see FIG. 5). The motor is sealed in the motor chamber 48 by a chamber wall 46, which separates the motor from the fan 47 but allows the motor to operate the fan 47.

Figure 7:
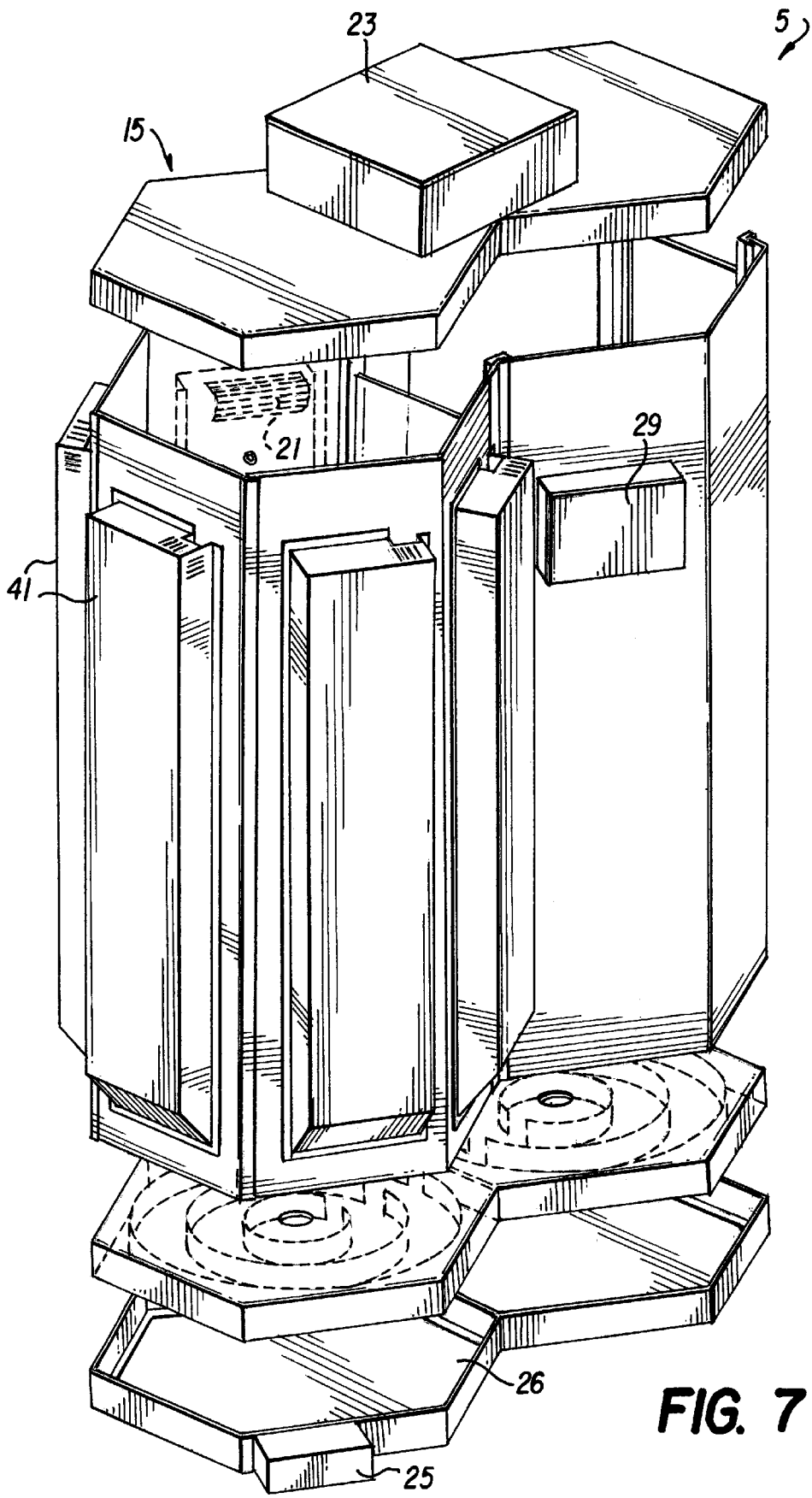
FIG. 7 is a expanded view of the booth.

As shown in FIGS. 6 and 7, the plenum housings 41 are positioned along the exterior of the wall panels of the spray chamber 15. The wall panels have vent openings 21 that permit the exhaust fan 47 to draw air and remnant mist into the plenum 41. The spray chamber 15 has a floor that is positioned over a frame with a basin 26 beneath the floor. Excess lotion and water pass through a drain in the floor of the chamber, into the basin 26, where a sump pump 25 passes it to waste. In addition, the mist that is condensed by the plenum 41 passes out of the bottom of the plenum 41 through openings in the wall panels, and into the basin 26. However, the plenum 41 can be alternatively configured so that the condensed mist can pass directly into the basin 26.

The exhaust fans 47 are activated in the drying mode to remove the remnants of the composition spray 19 left over during the spray mode. The exhaust fans 47 are located toward the top of the spray chamber 15, and draw in air and spray 19 to create an upward circulation of spray 19 that further facilitates a complete application of composition to the user. If the air were circulated downward, the user could obtain an incomplete coverage of composition spray 19.

In accordance with the preferred embodiment of FIG. 6, five plenums are provided about the spray chamber 15, one on each exterior wall panel, though any suitable number can be used. The ventilation system is able to exhaust the lotion spray within 30 seconds. The ventilation system and spray chamber 15 are sealed, so that mist does not pass outside the spray chamber 15. A heating and cooling unit can also be provided that allows the user to regulate the temperature of the composition and/or air.

The invention has been described as being implemented in a booth 5 having a dressing room 10 and a spray chamber 15. However, the spray chamber 15 need not be connected with a separate dressing room 10. Thus, the spray chamber 15 can be a room that is dedicated to coating the individual. For example, the spray chamber 15 can be used to apply a medical product for medical treatment of an injury or condition, such as the application of a burn lotion to treat a burn.

The spray chamber 15 is sealed to prevent the escape of water and spray. A control panel 29 is provided that permits the user to control operation of the ventilation system 9 and spray system 7, as well as the rinse and any other devices, such as dressing room lights.

The foregoing description and drawings should be considered as illustrative only of the principles of the invention. The invention may be configured is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

I claim:

1. A spray chamber for applying a composition to a user, the spray chamber comprising an enclosure having at least one wall surrounding the user, said at least one wall enclosing a spray area for receiving the user, stationary nozzles positioned about the spray area and stationary with respect to the spray area, and a compressor for forcing the composition through said stationary nozzles and directly into the spray area to provide an overlapping composition spray pattern in the spray area which completely coats the user with the composition.

2. The spray chamber of claim 1, wherein said compressor ceases forcing the composition through said stationary nozzles and forces air through said stationary nozzles into the spray area to dry the user.

3. The spray chamber of claim 1, further comprising a rinsing nozzle which emits a rinsing agent, said rinsing nozzle rinsing the spray chamber upon completion of the composition being emitted through said stationary nozzles.

4. The spray chamber of claim 1, further comprising a ventilation system having an exhaust fan for drawing air and remnant composition out of the spray chamber.

5. The spray chamber of claim 4, said ventilation system further comprising an air dam for preventing air from backdrafting.

6. The spray chamber of claim 4, said ventilation system further comprising a filter for condensing the remnant composition.

7. The spray chamber of claim 6, said ventilation system comprising a plenum containing the exhaust fan and the filter, the plenum directing the air and remnant composition drawn by the exhaust fan through the filter.

8. The spray chamber of claim 4, further comprising a pump for pumping the condensed remnant composition to waste.

9. The spray chamber of claim 1, wherein said compressor forces the composition through said stationary nozzles to completely coat the user in a single application.

10. The spray chamber of claim 1, wherein said compressor forces the composition through said stationary nozzles to completely coat the user as the user remains stationary.

11. The spray chamber of claim 1, wherein said compressor forces the composition through said stationary nozzles in the form of a mist.

12. The spray chamber of claim 1, wherein the spray area has a circular shape.

13. The spray chamber of claim 1, wherein said stationary nozzles are positioned substantially horizontally.

14. The spray chamber of claim 1, wherein said stationary nozzles are positioned along three vertical columns located about the spray area.

15. The spray chamber of claim 1, wherein the user stands in said enclosure.

16. A method for coating a user's body with a composition in a chamber, the method comprising:

defining a spray area in the chamber for receiving the user;

positioning stationary spray nozzles about the spray area; and, emitting the composition through the stationary spray nozzles and directly into the spray area to provide an overlapping composition spray pattern in the spray area to completely coat the user's body with the composition, wherein the stationary spray nozzles remain stationary with respect to the spray area as the composition is emitted through the stationary spray nozzles.

17. The method of claim 16, further comprising ceasing the emitting the composition and emitting air through the stationary spray nozzles to dry the user's body.

18. The method of claim 16, wherein the stationary spray nozzles completely coat the user's body in a single application.

19. The method of claim 16, wherein the stationary spray nozzles completely coat the user's body as the user's body remains stationary.

20. The method of claim 16, wherein the composition is emitted from said stationary spray nozzles in the form of a mist.

21. The method of claim 16, further comprising rinsing the spray chamber.

22. The method of claim 16, further comprising ventilating the chamber by drawing air and remnant composition from the chamber.

23. The method of claim 22, further comprising condensing the remnant composition.

24. The method of claim 22, further comprising pumping the condensed remnant composition to waste.

25. A spray chamber for applying a composition to a user, the spray chamber comprising:

at least one wall defining a spray area for receiving the user, the spray area having a front portion, a rear portion and two side portions;

stationary nozzles positioned about the spray area, and a compressor for forcing the composition through said stationary nozzles and directly into the spray area to provide an overlapping composition spray pattern at the front portion, rear portion and two side portions of the spray area, wherein said stationary nozzles are stationary with respect to the spray area as the composition is forced through said stationary nozzles.

26. The spray chamber of claim 25, wherein said compressor ceases forcing the composition through said stationary nozzles and forces air through said stationary nozzles into the spray area to dry the user.

27. The spray chamber of claim 25, wherein the spray area has a circular shape.

28. The spray chamber of claim 25, wherein said stationary nozzles are positioned substantially horizontally.

29. The spray chamber of claim 25, wherein said stationary nozzles are positioned along three vertical columns located about the spray area.

30. The spray chamber of claim 25, wherein the user stands in said enclosure.

31. The spray chamber of claim 25, further comprising a ventilation system having an exhaust fan for drawing air and remnant composition out of the spray chamber.

* * * * *